United States Patent [19]

Ohnishi et al.

[11] Patent Number: 4,495,282
[45] Date of Patent: Jan. 22, 1985

[54] PROCESS FOR PRODUCING TARGET CELL LYSIS FACTOR AND USES THEREWITH

[75] Inventors: Haruo Ohnishi, Chiba; Masakazu Mitsuhashi, Okayama, both of Japan

[73] Assignees: Kabushiki Kaisha Hayashibara Seibutsu Kagaku Kenkyujo, Okayama; Mochida Seiyaku Kabushiki Kaisha, Tokyo, both of Japan

[21] Appl. No.: 400,487

[22] Filed: Jul. 21, 1982

[30] Foreign Application Priority Data

| Jul. 21, 1981 | [JP] | Japan | 56-112913 |
| Jul. 21, 1981 | [JP] | Japan | 56-112914 |
| Jul. 31, 1981 | [JP] | Japan | 56-120459 |
| Nov. 21, 1981 | [JP] | Japan | 56-187626 |
| Nov. 21, 1981 | [JP] | Japan | 56-187627 |
| Dec. 21, 1981 | [JP] | Japan | 56-205115 |

[51] Int. Cl.$^3$ .................... C12P 21/00; A61K 39/100
[52] U.S. Cl. ........................ 435/68; 424/88; 260/112 R; 514/8
[58] Field of Search ............ 435/68, 240; 260/112 R; 425/85, 88; 424/177

[56] References Cited

U.S. PATENT DOCUMENTS

| 4,276,282 | 6/1981 | Sugimoto et al. | 424/85 |
| 4,296,025 | 10/1981 | Sugimoto | 260/112 R |
| 4,328,207 | 5/1982 | Sugimoto | 424/85 |
| 4,377,513 | 3/1983 | Sugimoto | 260/112 R |
| 4,383,034 | 5/1983 | Sugimoto | 435/70 |
| 4,383,035 | 5/1983 | Sugimoto | 435/70 |
| 4,383,036 | 5/1983 | Sugimoto | 435/70 |

OTHER PUBLICATIONS

Chemical Abstracts, vol. 94, Abstract No. 190193b, 1981.
Chemical Abstracts, vol. 94, Abstract No. 203547x, 1981.
Chemical Abstracts, vol. 92, Abstract No. 178942w, 1980.
Chemical Abstracts, vol. 89, Abstract No. 105663j, 1978.
Chemical Abstracts, vol. 87, Abstract No. 116322g, 1977.
Chemical Abstracts, vol. 87, Abstract No. 181370k, 1977.
Chemical Abstracts, vol. 84, Abstract No. 41845g, 1976.
Chemical Abstracts, vol. 79, Abstract No. 64453p, 1973.
Hashimoto, Y., "Target Cell Lysis and Lymphokines", in *Shin-Menekigaku Sosho*, vol. 6, Lymphokines, Igaku Shoin Ltd., Tokyo, Japan, (1979), edited by T. Kuroyanagi et al., pp. 87–105.
Bloom, B. R. et al., "In Vitro Methods in Cell-Mediated Immunity", Academic Press, Inc., (1971).
Carswell, E. A. et al., "An Exdotoxin–Induced Serum Factor that Causes Necrosis of Tumors", *Proc. Natl. Acad. Sci. USA*, vol. 72, #9, 3366–70, (1975).
M. R. Ruff, et al., "Tumor Necrosis Factor", in *Lymphokines*, edited by E. Pick, vol. 2, 235–272, Academ. Press, Inc., (1981).
Sato, *Protein, Nucleic Acid and Enzyme*, vol. 20, No. 6, 616–643, (1975).
J. E. Salk, *Journal of Immunology*, vol. 49, p. 87, (1944).

*Primary Examiner*—Blondel Hazel
*Attorney, Agent, or Firm*—Browdy and Neimark

[57] ABSTRACT

Target Cell Lysis Factor (TCLF) is produced by exposing a human cell line capable of producing TCLF to a TCLF inducer to induce TCLF production, and collecting and purifying the accumulated TCLF. The TCLF which is produced includes lymphotoxin and human Tumor Necrosis Factor (hTNF). The hTNF may be separated and purified. The human cell lines are preferably human leucocyte and human lymphoblastoid lines, such as BALL-1, TALL-1, NALL-1 Namalwa, MOLT-3, Mono-1, M-7002, B-7101, JBL, EBV-Sa, EBV-Wa, EBV-HO, BALM 2, CCRF-CEM, DND-41 and CCRF-SB, as well as human cell lines which are obtainable by transforming normal human monocytes, or granulocytes. All of these human cell lines are multipliable by implanting them in a non-human warm-blooded animal, or alternatively, allowing them to multiply in a conventional-type diffusion chamber by which the nutrient body fluid of a non-human warm-blooded animal is supplied to them.

23 Claims, No Drawings

PROCESS FOR PRODUCING TARGET CELL LYSIS FACTOR AND USES THEREWITH

DETAILED DESCRIPTION OF THE INVENTION

The present invention provides a process for producing Target Cell Lysis Factor (referred to as "TCLF" hereinafter), and to a therapeutic agent containing TCLF for use in the treatment of malignant tumors.

TCLF is defined throughout the present specification and claims as a factor which effects cytotoxicity on a mouse fibroblastoid line, L-929, as target cell, with its subsequent cytolysis. Two types of TCLF have been hitherto known, i.e., lymphotoxin and Tumor Necrosis Factor (referred to as "TNF" hereinafter), although the existence of human TNF has not previously been established.

As described in *Shin-Menekigaku Sosho*, Vol. 6, "Lymphokines", edited by T. Kuroyanagi et al and published by Igaku Shoin Ltd., Tokyo, Japan (1979), and B. R. Bloom and P. R. Glade, "*In Vitro Methods in Cell-Mediated Immunity*", published by Academic Press, Inc. (1971), lymphotoxin is the term given to a proteinaceous substance capable of effecting cytotoxicity which is intra- and/or extra-cellularly inducible, for example, by exposing either sensitized T-cells to an antigen, a nonsensitized T-cells to a lymphotoxin inducer, e.g., a mitogen such as phytohaemagglutinin or concanavalin A. It is well documented that lymphotoxin effects cytotoxicity on tumor cells as well as on normal cells.

As described by E. A. Carswell et al., *Proc. Natl. Acad. Sci. USA*, Vol. 72, No. 9, pp. 3666–3670 (1975), and M. R. Ruff et al "Tumor Necrosis Factor" in "Lymphokines", Vol. 2, edited by E. Pick, pp. 235–272 (1981), published by Academic Press, Inc., TNF is the term given to a proteinaceous substance which is inducible, for example, in macrophage, by parenterally administering to a rabbit a TNF inducer, such as, bacillus Calmette-Guerin (BCG), *Corynebacterium parvum*, or endotoxin; and which is capable of effecting hemorrhagic necrosis on Meth A sarcoma. Also it is well documented that TNF does not effect any practical cytolysis on normal human cells but, remarkably, effects cytolysis not only on the target mouse cell line, L-929, but also on human tumor cells.

The promise of TCLF as a therapeutic agent for the treatment of malignant tumors has produced a strong anticipation due to its cytolysis function on tumor cells.

Although there is no practical species-specificity for TCLF, which suggests the possibilities of using TCLF from non-human origin, e.g., rabbit or rat origin, in treating human diseases, the use of TCLF from viable human cells is desirable and very safe because it elicits less antigenicity and other side-effects when used in such treatment.

The present inventors have investigated various readily feasible industrial-scale processes for producing TCLF, and potential applications thereof as a therapeutic agent for malignant tumors.

These efforts have resulted in the findings that a great amount of TCLF may be easily obtainable by exposing human cells, obtained by multiplying a human cell line capable of producing TCLF, to a TCLF inducer to induce an enhanced TCLF production, and collecting and purifying the accumulated TCLF; and that the TCLF is excellent as a therapeutic agent for malignant tumors.

These findings have led to the present invention.

Also, the present inventors have found that the TCLF thus obtained comprises, at least, three types of glycoproteins with different molecular weights in the range of about $1 \times 10^4 - 1 \times 10^5$ daltons, which do not effect any practical cytolysis on normal human cells, but effect remarkable cytolysis on human tumor cells as well as the target mouse cell line, L-929.

The following descriptions explain the process for producing TCLF according to the present invention in further detail.

The human cell line usable in the present invention may be one of those which are multipliable in vitro according to conventional methods. In order to practice the present invention more efficiently, the use of human cells, which have been multiplied by transplanting said human cell line to a non-human warm-blooded animal, or, alternatively, allowing said human cell line to multiply in a conventional-type diffusion chamber by which the nutrient body fluid of a non-human warm-blooded animal is supplied to said cell line, is preferable. Unlike conventional processes wherein live human cells are multiplied in vitro, in addition to providing a much higher-titered TCLF, the process using the in vivo procedure requires no or much less nutrient medium, containing expensive serum, and render the maintenance of the culture during the cell multiplication much easier.

Although U.S. Pat. No. 4,276,282 (Sugimito et al.) discloses an improved process for producing human-specific interferon (referred to as "HuIFN" hereinafter) processing viral infection inhibitory activity, it does not teach any possibility of using a non-human warm-blooded animal for producing TCLF.

More particularly, in the process using a non-human warm-blooded animal as a host according to the present invention, certain human cell lines can be easily multiplied while utilizing the nutrient body fluid supplied from the non-human warm-blooded animal by transplanting them to the non-human warm-blooded animal, or, alternatively, placing them in a conventional-type diffusion chamber devised to receive the body fluid, and embedding or placing the chamber in or on the animal; and feeding the animal in the usual way.

Furthermore, the process according to the present invention is distinguishable from conventional in vitro cell multiplication methods using tissue culture by the facts that additional features, i.e., much more stabilized and rapid cell multiplication, higher cell production, and extremely higher TCLF production per cell, are attainable.

The human cell lines usable in the present invention may be those which are readily transplantable and multipliable in the animal, and which produce TCLF. For example, Namalwa, as described in *Journal of Clinical Microbiology*, Vol. 1, pp. 116–117 (1975); BALL-1, TALL-1 and NALL-1, as described by I. Miyoshi, *Nature*, Vol. 267, pp. 843–844 (1977); M-7002 and B-7101, as described in *Journal of Immunology*, Vol. 113, pp. 1334–1345 (1974); JBL, EBV-Sa, EBV-Wa, MOLT-3 and EBV-HO, as described in *The Tissue Culture*, Vol. 6, No. 13, pp. 527–546 (1980); CCRF-SB (ATCC CCL 120); BALM 2; DND-41; and other established cell lines obtained by transformation of normal monocytes or granulocytes using any carcinogenic virus, agent, or radiation.

Instead of using the above described cell lines, a human lymphoblastoid line which has had TCLF-production coding human genes introduced therein may be used. Such a line is much more readily subjectable to sub-culture. The human genes coding for TCLF-production may be introduced into the lymphoblastoid line by means of cell fusion using polyethylene glycol or Sendai virus, or by means of recombinant genetic engineering techniques using nuclease, ligase and DNA polymerase. Such lymphoblastoid lines result in an extreme increase in cell multiplication rate and/or TCLF production per cell. Accordingly, the listing of the human cell lines in the present specification will be intended in no way to limit the scope of the present invention.

It is also possible to use a combination of more than one of the above described cell lines in the present invention. Human leukocyte capable of producing TCLF, prepared from fresh human blood, may also be used in combination with the above described cell line(s).

The non-human warm-blooded animal usable in the present invention may be any one of those in which the cell line is multipliable; for example, fowl, such as chicken or pigeon; or mammalian, such as dog, cat, monkey, goat, rabbit, pig, horse, cow, guinea pig, rat, nude rat, hamster, mouse may be used, or nude mouse.

Since transplantation of such human cell line to the animal results in the elicitation of undesirable immunoreaction, in order to reduce the immunoreaction as much as possible, the use of a non-human warm-blooded animal in the possible youngest stage, e.g., egg, embryo, or foetus, or newborn or infant animal, is desirable.

Prior to the transplantation, such animal may be further treated with X-ray or $\gamma$-ray irradiation, about 200–600 rem, or injection of antiserum or immunosuppressant in order to reduce the immunoreaction to the lowest possible level.

When nude mouse or nude rat is used as the host animal, since the animal exhibits less undesirable immunoreaction even when in their adulthood, the animal can be readily transplanted with any of the above described cell lines without such pretreatment, and said cell line readily multiplies therein with less fear of causing undesirable immunoreaction.

One may obtain both stabilization of cell multiplication and augmentation of TCLF production by repeated transplantation using combinations of different non-human warm-blooded animals. For example, these objectives may be attained by first transplanting said cell line to a hamster and multiplying it therein, then retransplanting the multiplied human cells to a nude mouse. In this case, the repeated transplantation may be carried out with a non-human warm-blooded animal of differing species or genus in the same class or order, as well as with those of the same species or genus.

As to the site of the animal to which the cell line is transplantable, the cell line can be transplanted in any site of the animal so far as the cell line multiplies therein; for example, in the allantoic cavity, or intravenously, intraperitoneally, or subcutaneously.

Instead of transplanting the cell line to the animal, any of the hereinbefore described cell lines can be easily multiplied by placing it in a conventional-type diffusion chamber of various shapes and sizes equipped with, for example, a membrane filter, ultra-filter or hollow fiber of a nominal pore size of about $10^{-7}$–$10^{-5}$ m, which prevents contamination of the chamber with the animal cells, but supplies the cell line with the nutrient body fluid of the animal on which the chamber is embedded. The chamber is embedded, e.g., intraperitoneally, the chamber in the animal; and allowing the cell line to multiply therein while utilizing the nutrient body fluid supplied from the animal.

Furthermore, the diffusion chamber can be designed and placed, e.g., on the animal, so that the nutrient body fluid and nutrient solution in the chamber can freely circulate through the chamber. In this way, the culture in the chamber can be observed during the cell multiplication through transparent side window(s), equipped on the chamber wall(s), and/or the chamber can be continually replaced with a fresh one, both to continue the cell multiplication over the period of its life span without sacrificing and to augment much more the cell production per animal.

Since the use of such diffusion chamber does result in less elicitation of undesirable immunoreaction due to the absence of direct contact of the human cells with the animal cells, any non-human warm-blooded animal may be readily used as the host without pretreatment, and the multiplied live human cells can be easily harvested therefrom.

Feeding of the animal can be easily carried out in usual way, and no special care is not required even after the transplantion.

The period required to obtain maximum cell multiplication is generally within 1 to 10 weeks. The number of the human cells thus obtained may be about $10^7$–$10^{12}$ per animal or higher. Strictly, according to the present invention, the transplanted human cells increase about $10^2$–$10^7$-fold or higher, which is about $10$–$10^6$-fold higher than that obtained by in vitro multiplication procedures using nutrient medium; thus, the multiplied human cells are preferably usable for the present objectives.

Any method by which the multiplied human cells are induced to produce TCLF can be employed in the invention. One such method is to expose the multiplied human cells to a TCLF inducer while still in the animal used as the host for cell multiplication. For example, human cells, multiplied in ascite in suspension, or tumor cells, formed, e.g., subcutaneously, may be directly exposed in vivo to a TCLF inducer to induce TCLF production, and the accumulated TCLF harvested from the ascite, serum and/or tumor, followed by purification of the TCLF.

Alternatively, the multiplied human cells may be harvested from the animal and then exposed in vitro to a TCLF inducer. For example, the multiplied human cells, obtained by harvesting from ascite suspension, or extracting and disaggregating the massive tumor(s), formed, e.g., subcutaneously, are suspended in a nutrient medium, prewarmed to a temperature in the range of about 20°–40° C., to give a cell density of about $10^5$–$10^8$ cells per ml, and exposed in vitro to a TCLF inducer, followed by the collection of the accumulated TCLF from the culture.

When the human cell line is multiplied in a conventional-type diffusion chamber, the multipled human cells can be exposed to a TCLF induces either in the chamber or after harvest therefrom.

The human cells thus obtained may be further cultivated in vitro for an additional 1–4 days to regulate the generation time prior to the TCLF induction.

The TCLF production per animal may be further augmented by employing any of the following methods:
  (1) the multiplied human cells are exposed to a TCLF inducer in the animal which has been used as the host for cell multiplication, and the human cells are then harvested from certain site(s) of the animal or its whole body, followed by in vitro re-exposure of the human cells to a TCLF inducer,
  (2) the human cells are repeatedly exposed in vitro and/or in vivo to a TCLF inducer, and/or
  (3) the diffusion chamber, which has been embedded in the animal or placed thereon, is continually replaced with a fresh one.

The TCLF inducer usable in the present invention may be one or more members of those which induce TCLF production in the human cells obtained by multiplying the human cell line while utilizing the nutrient body fluid supplied from the animal. For example, any conventional α-interferon inducer (IFN-α inducer), such as virus, nucleic acid or nucleotide; or γ-interferon inducer (IFN-γ inducer), such as, phytohaemagglutinin, concanavalin A, pokeweed mitogen, lipopolysaccharide, endotoxin, polysaccharide, or bacteria, is usable as the TCLF inducer. Generally, the use of an IFN-α inducer is preferable because TCLF with a much higher titer can be induced therewith.

Certain antigens act as TCLF inducer on cells which have been sensitized with the antigen.

It has been confirmed that the combination of both IFN-α-and IFN-γ inducers as TCLF inducer advantageously results in a remarkable augmentation of the induced TCLF production.

It has also been confirmed that such a combination leads to the simultaneous production of HuIFN.

This confirmation suggests that the use of such inducers enables a simultaneous and low-cost mass-production of two or more biologically-active substances, i.e., invaluable TCLF and HuIFN, as well as enables a much more effective utilization of the multiplied human cells.

The TCLF thus obtained can be easily collected by purification and separation methods using conventional procedures, e.g, concentration, salting-out, dialysis, filtration, centrifugation, and/or lyophilization. If a more purifed TCLF preparation is desirable, a preparation of the highest possible purity can be obtained by the above described procedures in combination with other conventional procedures, e.g., adsorption and desorption with ion exchanger, gel filtration, electrophoresis and/or isoelectric point fractionation.

Instead of using the above described procedure, the use of affinity chromatography, using either an antibody or a mitogen as a ligand, e.g., Con A-Sepharose, a product of Pharmacia Fine Chemicals AB, Uppsala, Sweden, may attain a more speedy and easier production of high-purity TCLF.

It has been confirmed that the TCLF thus obtained substantially consists of three glycoproteins with different molecular weights of about $1\times10^4$–$2\times10^4$ daltons, about $3.5\times10^4$–$5\times10^4$ daltons and about $7\times10^4$–$9\times10^4$ daltons, which do not effect any practical cytolysis on normal human cells, but effect remarkable cytolysis on human tumor cells as well as on the mouse cell line, L-929. Thus, TCLF is preferably usable as a prophylactic- and/or therapeutic agent for TCLF-sensitive diseases, e.g., malignant tumor, treatment of which has previously been deemed to be very difficult.

Throughout the present specification, the TCLF titers were assayed by either the lymphotoxin assay method as reported by B. R. Bloom and P. R. Glade, "In Vitro Methods in Cell-Mediated Immunity", published by Academic Press, Inc. (1971), or the TNF assay method as reported by M. R. Ruff, et al, "Tumor Necrosis Factor" in "Lymphokines", Vol. 2, pp. 235–272, edited by E. Pick and published by Academic Press, Inc. (1981), wherein the mouse cell line, L-929, is incubated in the presence of TCLF for a certain period, and the surviving cells are counted.

The titers of HuIFN were assayed by the conventional plaque-reduction method using FL-cells of human amnion origin as described in *Protein, Nucleic Acid and Enzyme*, Vol. 20, No. 6, pp. 616–643 (1975).

The haemagglutination titers were assayed by the method as reported by J. E. Salk, *Journal of Immunology*, Vol. 49, page 87 (1944) with a slight modification.

The following EXPERIMENT A explains the production of lymphotoxin, one type of TCLF.

EXPERIMENT A

Lymphotoxin-producibility of human cells multiplied in vitro or in vivo

EXPERIMENT A-1

In vitro cell multiplication

A human lymphoblastoid line of B-cell origin, BALL-1, was transplanted into RPMI 1640 medium (pH 7.2), supplemented with 20 v/v % foetal calf serum, and cultivated in suspension at 37° C. The multiplied human cells were washed with serum-free RPMI 1640 medium (pH 7.2), and then resuspended in a fresh medium of the same composition to give a cell density of about $1\times10^6$ cells per ml.

EXPERIMENT A-2

In vivo cell multiplication

After injecting newborn hamsters with antiserum, prepared from rabbit in the usual way, to reduce their immunoreactions, the animals were subcutaneously transplanted with a human lymphoblastoid line of B-cell origin, BALL-1, and then fed in the usual way for three weeks. The resultant massive tumors, formed subcutaneously, were extracted and disaggregated by suspending in a physiological saline solution containing trypsin. Then, the cells were washed with serum-free RPMI 1640 medium (pH 7.2), and resuspended in a fresh medium of the same composition to give a cell density of about $1\times10^6$ cells per ml.

EXPERIMENT A-3

Lymphotoxin production

Lymphotoxin induction was carried out in each cell suspension of the multiplied BALL-1 cells, prepared in Experiments A-1 and A-2, using Sendai virus and/or phytohaemagglutinin. To each of the cell suspensions was added Sendai virus and/or phytohaemagglutinin in respective amounts of about 300 haemagglutination titers per ml and/or about 50 μg per ml, and the mixtures were incubated at 37° C. for two days to induce TCLF production. After the incubation, simultaneous large-productions of HuINF-α and HuINF-γ were noted in the culture, as well as the production of lymphotoxin.

TABLE I gives the results of lymphotoxin production.

TABLE I

| Lymphotoxin inducer | Cell multiplication | |
|---|---|---|
| | In vitro | In vivo |
| Sendai virus (IFN-α inducer) | 300 (1,600) | 4,000 (7,000) |
| Phytohaemagglutinin (IFN-γ inducer) | 160 (20) | 2,200 (400) |
| Sendai virus plus Phytohaemagglutinin | 900 (1,700) | 38,000 (26,000) |

Note:
The values show the lymphotoxin titers per ml; and those in parenthesis, HuIFN titers per ml.

As obvious from the experimental results shown in Table I, lymphotoxin is produced in the human cells multiplied in vitro, as well as in those multiplied in vivo. The amount of lymphotoxin induced in the latter is, however, much higher, i.e., about 10-fold or higher, than that induced in the former. The lymphotoxin production with the use of Sendai virus is comparable to or higher than that attained with the use of phytohaemagglutinin. The use of both Sendai virus and phytohaemagglutin synergistically enhances the lymphotoxin production in the human cells regardless of the multiplication procedures in comparison with those using Sendai virus or phytohaemagglutinin. The synergistic effect is much more remarkable in the human cells multiplied in vivo than in those multiplied in vitro.

From the above descriptions, it can be concluded that the use of a highly-specific IFN inducer, particularly the, combination of IFN-α and IFN-γ inducers, is preferable for induction of non-species-specific lymphotoxin.

The following EXAMPLEs illustrate the production of lymphotoxin and TNF, two types of TCLF, according to the present invetion.

EXAMPLE A-1

After injecting antiserum, prepared from rabbit according to conventional methods, into newborn hamsters to reduce their immunoreaction, the animals were subcutaneously transplanted with a human lymphoblastoid line, BALL-1, and fed in the usual way for three weeks.

The resultant massive tumors, formed subcutaneously, about 15 g each, were extracted, minced, and disaggregated by suspending in a physiological saline solution containing trypsin.

The human cells thus obtained were washed with serum-free RPMI 1640 medium (pH 7.2), and resuspended in a fresh medium of the same composition to give a cell density of about $5 \times 10^6$ cells per ml. To the cell suspension was added both Sendai virus and phytohaemagglutinin in respective amounts of about 1,000 haemagglutination titers per ml and about 200 μg per ml, and the mixture was then incubated at 37° C. for two days to induce lymphotoxin production.

Thereafter, the culture was centrifuged at 4° C. and at about $1,000 \times g$, and the supernatant was dialyzed against a physiological saline solution containing 0.01M phosphate buffer (pH 7.2) for 21 hours. The resultant solution, possessing lymphotoxin activity, was then filtered with the use of a membrane filter, and the filtrate was concentrated, and lyophilized to obtain a powder product.

The lymphotoxin yield was about $5 \times 10^7$ units per hamster. The powder also contained about $3.2 \times 10^7$ units of HuIFN.

EXAMPLE A-2

A human lymphoblastoid line, BALL-1, was inoculated to Eagle's minimal essential medium (pH 7.4), supplemented with 20 v/v % foetal calf serum, and cultivated therein in vitro in suspension at 37° C. After washing the multiplied human cells with serum-free Eagle's minimal essential medium (pH 7.4), the cells were resuspended in a fresh medium of the same composition to give a cell density of about $1 \times 10^7$ cells per ml. Thereafter, to the cell suspension was added both Sendai virus and concanavalin A in respective amounts of about 1,000 haemagglutination titers per ml and about 5 μg per ml, and the mixture was incubated at 38° C. for one day to induce lymphotoxin production.

After centrifuging the culture at 4° C. and at about $1,000 \times g$, the supernatant was dialyzed against a physiological saline solution containing 0.01M phosphate buffer (pH 7.2) for 15 hours. The resultant solution was filtered with the use of a membrane filter, and the filtrate, possessing a lymphotoxin activity, was concentrated.

The lymphotoxin yield was about $4.5 \times 10^6$ units in terms of one liter cell suspension upon the induction. The HuIFN yield was about $1.2 \times 10^7$ units per liter cell suspension.

EXAMPLE A-3

Adult nude mice were intraperitoneally transplanted with a human lymphoblastoid line of B-cell origin, Namalwa, and fed in the usual way for five weeks. Thereafter, the animals were intraperitoneally injected with UV-irradiation preinactivated Newcastle disease virus in an inoculum of about 3,000 haemagglutination titers per animal, and sacrificed 24 hours after the injection, followed by ascite-harvesting.

Similarly as in EXAMPLE A-1, the ascites were purified, and concentrated to obtain a powder possessing a lymphotoxin activity.

The lymphotoxin yield was about $9 \times 10^6$ units per animal. The powder also contained about $5.2 \times 10^6$ units of HuIFN.

EXAMPLE A-4

After irradiating adult mice with X-ray, about 400 rem, to reduce their immunoreactions, the animals were subcutaneously transplanted with a human lymphoblastoid line of B-cell origin, CCRF-SB, and fed in the usual way for three weeks.

The resultant massive tumors, formed subcutaneously, about 10 g each, were extracted, and disaggregated similarly as in EXAMPLE A-1. The human cells thus obtained were suspended in a fresh medium of the same composition as used in EXAMPLE A-1, and the cell suspension was added with Sendai virus and concanavalin A in respective amounts of about 500 haemagglutination titers per ml and about 0.8 μg per ml, followed by 1-day incubation of the cell suspension at 37° C. to induce lymphotoxin production.

Similarly as in EXAMPLE A-1, the culture was purified, and concentrated to obtain a powder product possessing a lymphotoxin activity.

The lymphotoxin yield was about $2.4 \times 10^7$ units per mouse. The powder also contained about $1.9 \times 10^7$ units of HuIFN.

EXAMPLE A-5

Similarly as in EXAMPLE A-1, newborn hamsters were transplanted with a human lymphoblastoid line, JBL, and then fed in usual way for four weeks.

The resultant massive tumors, formed subcutaneously, about 20 g each, were disaggregated similarly as in EXAMPLE A-1 to obtain a cell suspension with a cell density of about $3 \times 10^6$ cells per ml. To the cell suspension was added Sendai virus in an amount of about 1,000 haemagglutination titers per ml, and the mixture was then incubated at 36° C. for two days to induce lymphotoxin production.

The culture was purified, and concentrated similarly as in EXAMPLE A-2 to obtain a concentrate possessing a lymphotoxin activity.

The lymphotoxin yield was about $1.6 \times 10^7$ units per hamster. The concentrate also contained about $7 \times 10^6$ units of HuIFN per hamster.

EXAMPLE A-6

A human lymphoblastoid line of B-cell origin, EBV-HO, was suspended in physiological saline solution, and the resultant suspension was then placed in a plastic cylindrical diffusion chamber with about 10 ml inner volume, equipped with a membrane filter having a nominal pore size of about 0.5 $\mu$, followed by intraperitoneal embedding of the chamber into an adult rat.

The animal was then fed in the usual way for four weeks, and the chamber was removed therefrom.

The cell density of the multiplied human lymphoblastoid cells in the chamber obtained by the above procedure was about $6 \times 10^8$ cell per ml, which was about $10^2$-fold or higher than that obtained by in vitro method with a $CO_2$ incubator using a nutrient medium.

The human cells thus obtained were suspended similarly as in EXAMPLE A-2, and the cell suspension was added with a thermally-preinactivated Newcastle disease virus and phytohaemagglutinin in respective amounts of about 500 haemagglutination titers per ml and about 100 $\mu$g per ml, followed by 2-day incubation of the cell suspension at 37° C. to induce lymphotoxin production.

The culture was purified, and concentrated similarly as in EXAMPLE A-1 to obtain a powder product possessing a lymphotoxin acitivity.

The lymphotoxin yield was about $5.4 \times 10^6$ units per rat. The powder also contained about $6.8 \times 10^6$ units of HuIFN.

EXAMPLE A-7

A human lymphoblastoid line, BALL-1, was transplanted in the allantoic cavities of embryonated eggs which had been preincubated at 37° C. for five days, and the eggs were further incubated at this temperature for an additional one week. The multiplied human cells were harvested from the eggs, and suspended similarly as in EXAMPLE A-1 to give a cell density of $5 \times 10^6$ cells per ml.

The cell suspension was added Sendai virus in an amount of about 1,000 haemagglutination titers per ml, and was incubated at 37° C. for one day to induce lymphotoxin production. Thereafter, the culture was purified, and concentrated similarly as in EXAMPLE A-2 to obtain a concentrate possessing a lymphotoxin activity.

The lymphotoxin yield was about $9 \times 10^5$ units per 10 embryonated eggs. The powder product also contained about $3.5 \times 10^5$ units of HuIFN per 10 embryonated eggs.

EXAMPLE A-8

Similarly as in EXAMPLE A-4, a human lymphoblastoid line, MOLT-3, was treated in place of the human lymphoblastoid line, CCRF-SB, to obtain a powder product possessing a lymphotoxin activity.

The lymphotoxin yield was about $3.3 \times 10^7$ units per mouse. The powder product also contained about $1.4 \times 10^7$ units of HuIFN.

EXAMPLE A-9

The HuIFN constituent in a powder product, obtained similarly as in EXAMPLE A-1, was removed by adsorption and desorption with ion exchanger, molecular weight fractionation using gel filtration, concentration, and filtration using a membrane filter, according to the method as reported by G. Bodo, "Symposium on Preparation, Standardization and Clinical Uses of Interferon" 11-th International Immunobiological Symposium, 8 & 9 June 1977, Zagreb, Yugoslavia, and the resultant HuIFN-free product was concentrated, and purified by salting-out using ammonium sulfate. The resultant was then subjected to affinity-chromatography using phytohaemagglutinin-Sepharose in 0.01M phosphate buffer (pH 7.4), and the adsorbed part was eluted by charging thereto a fresh preparation of the same buffer, containing additionally 0.1M N-acetyl-D-galactosamine. The eluted fractions possessing a lymphotoxin activity were dialyzed against a fresh preparation of the same buffer but without N-acetyl-D-galactosamine, concentrated, and lyophilized to obtain a powder product.

The specific activity of the lymphotoxin thus obtained was about 30,000 units per mg protein.

Gel filtration of the powder product according to molecular weight gave the following results: The product was separated into three constituents with different molecular weights of about $7 \times 10^4 - 9 \times 10^4$ daltons, about $3.5 \times 10^4 - 5 \times 10^4$ daltons, and about $1 \times 10^4 - 2 \times 10^4$ daltons, in an activity ratio of about 1:1:2, which should be correspondent with the reported $\alpha$-, $\beta$- and $\gamma$-lymphotoxins, respectively, in view of their molecular weights and other available physicochemical information. All constituents were glycoproteins, and the saccharide contents thereof fell in the range of abot 5–45%, dependent upon their molecular weights.

EXAMPLE A-10

Newborn hamsters were injected with antiserum, prepared from rabbit in the usual way, to reduce their immunoreaction as much as possible, and then subcutaneously transplanted with a human cell line of monocytic origin transformed with the use of SV-40 virus, followed by one-week of feeding in the usual way. Then, the animals were intraperitoneally injected with live BCG cells in a inoculum of $10^7$ cells per animal, and fed for an additional two weeks.

Thereafter, the resultant massive tumors, formed subcutaneously, about 15 g each, were extracted, minced, and disaggregated by suspending in a physiological saline solution containing trypsin. After washing the human cells with Eagle's minimal essential medium (pH 7.2), supplemented with 5 v/v % human serum, the cells were suspended in a fresh medium of the same composition to give a cell density of about $5 \times 10^6$ cells per ml. Then, to the cell suspension was added E. coli endotoxin in an amount of about 10 μg per ml, and incubated at 37° C. for 16 hours to induce TNF production.

Thereafter, the culture was centrifuged at 4° C. and at about 1,000×g, to remove the precipitate, and the remaining supernatant was dialyzed against a physiological saline solution containing 0.01M phosphate buffer (pH 7.2) for 21 hours. The resultant solution was then filtered with the use of a membrane filter, and the filtrate, possessing a TNF activity, was lyophilized to obtain a powder product.

The HuIFN constituent in the powder product was removed by means of adsorption and desorption with ion exchanger, molecular weight fractionation using gel filtration, concentration and filtration using a membrane filter, according to the method as described by G. Bodo, "Symposium on Preparation, Standardization and Clinical Use of Interferon", 11-th International Immunobiological Symposium 8 & 9 June (1977), Zagreb, Yugoslavia, and the resultant HuIFN-free product was purified by means of salting-out using ammonium sulfate, and affinity chromatography using Con A-Sepharose, a product of Pharmacia Fine Chemicals AB, Uppsala, Sweden, obtaining about $1 \times 10^6$ units of a high-purity TNF capable of effecting cytolysis on Meth A sarcoma but not effecting any practical cytolysis on human normal cells while remarkably effecting cytalysis on human tumor cells.

The TNF thus obtained was free from the TNF inducer, and the specific activity thereof was about 350,000 units per mg protein.

EXAMPLE A-11

After injecting antiserum, prepared from rabbit in the usual way, into newborn hamsters to reduce their immunoreaction, the animals were subcutaneously transplanted with a human lymphoblastoid line, BALL-1, and fed in usual way for three weeks.

After extracting and mincing the resultant massive tumors, formed subcutaneously, about 15 g each, the resultant was disaggregated by suspending in a physiological saline solution containing trypsin. After washing the human cells with serum-free RPMI 1640 medium (pH 7.2), the human cells were resuspended in a fresh medium of the same composition to give a cell density of about $1 \times 10^7$ cells per ml.

To the cell suspension was added Sedai virus and $E.$ $coli$ endotoxin in respective amounts of about 1,000 haemagglutination titers per ml and about 20 μg per ml, followed by two-day incubation of the cell suspension at 37° C. to induce TNF production.

Thereafter, the culture was centrifuged at 4° C. and at about 1,000×g, to remove the precipitate, and the remaining supernatant was dialyzed against a physiological saline solution containing 0.01M phosphate buffer (pH 7.2) for 21 hours, followed by filtration of the resultant solution with the use of a membrane filter. Then, the filtrate possessing a TNF activity was concentrated, and lyophilized to obtain a powder product.

The TNF yield was about $8.3 \times 10^7$ units per hamster. The product also contained about $4.1 \times 10^7$ units of HuIFN.

EXAMPLE A-12

Adult nude mice were intraperitoneally transplanted with a human lymphoblastoid line, TALL-1, and fed in usual way for five weeks. Thereafter, the animals were intraperitoneally injected with a UV-irradiation preinactivated Newcastle disease virus in an inoculum of about 3,000 haemagglutination titers per animal, and sacrificed 24 hours after the injection, followed by ascite-harvesting.

The ascites were purified, concentrated, and dried similarly as in EXAMPLE A-11 to obtain a powder product possessing a TNF activity. The TNF yield was about $6.2 \times 10^6$ units per nude mouse. The product also contained about $4.5 \times 10^6$ units of HuIFN.

EXAMPLE A-13

After irradiating adult mice with X-ray, about 400 rem, to reduce their immunoreactions, the animals were subcutaneously transplanted with a human cell line, Mono-1, and fed in the usual way for three weeks.

Thereafter, the resultant massive tumors, formed subcutaneously, about 10 g each, were extracted, minced, and disaggregated similarly as in Example A-10.

Thereafter, the human cells were resuspended in a fresh medium of the same composition as used in Example A-10 to give the same cell density. To the cell suspension was added concanavalin A and Sendai virus in respective amounts of 0.8 μg per ml and about 500 haemagglutination titers per ml, followed by one-day incubation of the resultant mixture at 37° C. to induce TNF production.

The resultant culture was then purified, concentrated, and dried similarly as in EXAMPLE A-11 to obtain a powder product possessing a TNF activity.

The TNF yield was about $6.8 \times 10^7$ unite per mouse. The powder product also contained about $1.3 \times 10^7$ units of HuIFN.

EXAMPLE A-14

Newborn hamsters were transplanted similary as in EXAMPLE A-10 with a human lymphoblastoid line, Namalwa, and then fed in the usual way for four weeks.

Similarly as in Example A-11, the resultant massive tumors, formed subcutaneously, about 20 g each, were extracted, minced, and disaggregated similarly as in the same EXAMPLE to obtain a cell suspension with a cell density of about $3 \times 10^6$ cells per ml. Then, the cell suspension was added Sendai virus in an amount of about 1,000 haemagglutination titers per ml, and then incubated at 36° C. for two days to induce TNF production. Thereafter, the culture was purified, and concentrated similarly as in EXAMPLE A-11 to obtain a concentrate possessing a TNF activity.

The TNF yield was about $4.3 \times 10^7$ units per hamster. The product also contained about $8.2 \times 10^6$ units of HuIFN.

EXAMPLE A-15

After suspending a human lymphoblastoid line, NALL-1, in physiological saline solution, the cell suspension was placed in a plastic cylindrical diffusion chamber with an about 10 ml inner volume, equipped with a membrane filter having a nominal pore size of about 0.5μ, and the chamber was intraperitoneally embedded in an adult rat.

The animal was then fed in the usual way for four weeks, and the chamber was removed therefrom.

The cell density in the chamber thus obtained was about $5 \times 10^8$ cells per ml, which was about $10^2$-fold higher than that obtained in in vitro tissue culture method with a $CO_2$ incubator using a nutrient medium.

The multiplied human cells were resuspended in a fresh medium of the same composition as used in EXAMPLE A-10 to give the same cell density, and the resultant cell suspension was added with a UV-irradiation-preinactivated Newcastle disease virus and phytohaemagglutinin in respective amounts of about 500 haemagglutination titers per ml and about 100 μg per ml, followed by 2-day incubation of the cell suspension at 37° C. to induce TNF production.

Thereafter, the culture was purified, concentrated, and dried similarly as in EXAMPLE A-11 to obtain a powder product possessing a TNF activity.

The TNF yield was about $2.6 \times 10^7$ units per rat. The powder product also contained about $9.4 \times 10^6$ units of HuIFN.

EXAMPLE A-16

A human lymphoblastoid line, JBL, was transplanted in the allantoic cavities of embryonated eggs, which had been incubated at 37° C. for five days, and the eggs were further incubated at this temperature for an additional one week.

Thereafter, the multiplied human cells were suspended in a fresh medium of the same composition as used in EXAMPLE A-10 to give a cell density of $5 \times 10^6$ cells per ml. The cell suspension was then added with Sendai virus in an amount of about 1,000 haemagglutination titers per ml, and incubated at 37° C. for one day to induce TNF production. The culture was then purified, and concentrated similarly as in EXAMPLE A-11 to obtain a concentrate possessing a TNF activity.

The TNF yield was about $1.5 \times 10^6$ units per 10 embryonated eggs, and the available physicochemical properties were in good agreement with those reported by Carswell et al., supra The concentrate also contained about $4.0 \times 10^5$ units of HuIFN per 10 embryonated eggs.

The present TCLFs obtained in the above embodiments are advantageously feasible as prophylactic- and/or therapeutic agents for TCLF-sensitive diseases, e.g., in the form of injection solution, agent for internal or external administration, collyrium or collunarium, alone or in combination with one or more other agents.

The term "TCLF-sensitive disease", as used in the present specification, shall mean all human diseases which can be prevented and/or treated with the use of TCLF; for example, malignant tumors, such as breast cancer, lung carcinoma, uterine cancer, urinary bladder cancer, colon carcinoma, stomach cancer, leukaemia, lymphoma, and skin carcinoma.

The following Experiments B and C explain the efficacy, toxicity, instructions, and dosage of the present TCLF.

EXPERIMENT B

Efficacy and toxicity of TNF

EXPERIMENT B-1

BALB/C nude mice were subcutaneously transplanted in their dorsum area with small fragments of human breast cancer tissue.

After growing the resultant massive tumors to about 200 mm³, the TNF preparation aliquots, obtained in EXAMPLE A-10, were intravenously injected every day in a dosage of either 100 units/kg/day or 1,000 units/kg/day. Fifteen days after the first injection the animals were sacrificed, and the resultant massive tumors were weighed. The results are given in TABLE II. A TNF-free physiological saline solution was intravenously injected as a control.

TABLE II

| Treatment | Dosage per day | Wet weight of massive tumor (g) |
|---|---|---|
| Control | | 11.0 ± 1.4 |
| T N F | 100 units/kg | 7.5 ± 0.8 |
| T N F | 1,000 units/kg | 7.1 ± 0.4* |

Note:
*means the value is statistically significant against the control in a level of significance of 5%.

EXPERIMENT B-2

Groups of 10 male BDF₁ mice per group, about 25 g each mouse, were subcutaneously transplanted in their dorsum area with 2 mm squares of Lewis's lung carcinoma tissue. After a lapse of 8 days after the transplantation, the animals were intravenously injected every day with the TNF, obtained in EXAMPLE A-10, in a dosage of either 100 units/kg/day or 1,000 units/kg/day. Twenty-one days after the first injection, the animals were sacrificed, and the resultant massive tumors were weighed. The results are given in TABLE III. A TNF-free physiological saline solution was intravenously injected as a control.

TABLE III

| Treatment | Dosage per day | Wet weight massive tumor (g) |
|---|---|---|
| Control | | 7.5 ± 0.5 |
| T N F | 100 units/kg | 6.7 ± 0.8 |
| T N F | 1,000 units/kg | 4.5 ± 0.4* |

Note:
*means the value is statistically significant against the control in a level of significance of 5%.

EXPERIMENT B-3

An acute toxicity test on the TNF preparation obtained in EXAMPLE A-10, using 20-day old mice confirmed that the toxicity of the TNF preparation is extremely low, i.e., LD₅₀, 200,000 units/kg or higher, upon intraperitoneal injection.

The following EXPERIMENT C explains the efficacy, toxicity, instructions, and dosage of lymphotoxin, another type of TCLF.

EXPERIMENT C

EXPERIMENT C-1

BALB/C nude mice were subcutaneously transplanted in their dorsum area with small fragments of human breast cancer tissue.

After growing the resultant massive tumors to about 200 mm³, lymphotoxin mixture aliquots containing lymphotoxin specimens with molecular weights of $7 \times 10^4$–$9 \times 10^4$ daltons, $3.5 \times 10^4$–$5 \times 10^4$ daltons, and $1 \times 10^4$–$2 \times 10^4$ daltons, obtained similarly as in EXAMPLE A-9, were intravenously injected twice every day in a dosage of either 4 units/kg/day or 40 units/kg/day. Fifteen days after the first injection, the animals were sacrificed, and the resultant massive tumors were weighed. The results are given in TABLE IV. A Lymphotoxin-free physiological saline solution was intravenously injected as a control.

TABLE IV

| Treatment | Dosage per day | Wet weight of massive tumor (g) |
| --- | --- | --- |
| Control | | 10.8 ± 1.2 |
| Lymphotoxin mixture | 4 units/kg | 7.9 ± 0.7 |
| Lymphotoxin mixture | 40 units/kg | 7.4 ± 0.5* |

Note:
*means the value is statistically significant against the control in a level of significance of 5%.

EXPERIMENT C-2

Groups of 10 male BDF$_1$ mice per group, about 25 g each mouse, were subcutaneously transplanted in their dorsum area with 2 mm squares of Lewis's lung carcinoma tissue. After a lapse of 8 days after the transplantation, the animals were intravenously injected twice every day with either a lymphotoxin mixture or $\gamma$-lymphotoxin preparation with a molecular weight of $1 \times 10^4 - 2 \times 10^4$ daltons, both obtained in EXAMPLE A-9, in a dosage of either 4 units/kg/day or 40 units/kg/day. Twenty one-days after the first injection, the animals were sacrificed, and the resultant massive tumors were weighed. The results are given in TABLE V. A lymphotoxin-free physilogical saline solution was intravenously injected as a control.

TABLE V

| Treatment | Dosage per day | Wet weight massive tumor (g) |
| --- | --- | --- |
| Control | | 7.3 ± 0.3 |
| Lymphotoxin mixture | 4 units/kg | 6.6 ± 0.7 |
| Lymphotoxin mixture | 40 units/kg | 4.7 ± 0.5* |
| $\gamma$-Lymphotoxin ($1 \times 10^4 - 2 \times 10^4$ daltons) | 4 units/kg | 6.1 ± 0.6 |
| $\gamma$-Lymphotoxin ($1 \times 10^4 - 2 \times 10^4$ daltons) | 40 units/kg | 4.2 ± 0.4* |

Note:
*means the value is statistically significant against the control in a level of significance of 5%.

EXPERIMENT C-3 groups of 20 male BDF$_1$ mice per group, about 25 g each mouse, were subcutaneously transplanted with a mouse leukaemic line, L-1210, in their dorsum area. From the day following transplantation, the animals were intravenously injected one or twice every day with a dosage of either 30 units/kg/day or 300 units/kg/day to determine the period required for 50% survival.

Either a lymphotoxin-free physiological saline solution or mitomycin C, dosage, 0.5 mg/kg/day, was intravenously injected as a control. The results are given in TABLE VI.

TABLE VI

| | Treatment | Once per day | Twice per day |
| --- | --- | --- | --- |
| Control | Saline | 9 day | 9 day |
| | Mitomycin C (0.5 mg/kg/day) | 9 day | 9 day |
| Lymphotoxin mixture | 30 units/kg/day | 9 day | 15 day |
| | 300 units/kg/day | 12 day | 16 day |

The experimental results, as shown in TABLE VI, confirms that despite the dosage of the lymphotoxin mixture being relatively small, a much more effective treatment can be expected by increasing the frequency of daily dosage from once to twice.

EXPERIMENT C-4

Groups of 20 male BDF$_1$ mice per group, about 25 g each mouse, were transplanted with a cell line of mouse leukaemia origin, P 388. From the day following transplantation, the animals were intravenously injected every day with the lymphotoxin mixture for 30 days to determine the relationship between the dosage and days of survival or survival ratio (%).

Either a lymphotoxin-free physiological saline solution, or mitomycin C, dosage, 0.5 mg/kg/day, was intravenously injected as a control.

TABLE VII gives the results.

As obvious from the experimental results in TABLE VII, administration in large dosage, i.e., 1,000 units/kg/day or more, is much more effective when the lymphotoxin mixture is used as prophylactic- or therpaeutic agent.

TABLE VII

| | | Days of survival | | | | |
| --- | --- | --- | --- | --- | --- | --- |
| Treatment | | 1 | 6 | 15 | 30 | 80 |
| Control | Saline | 100% | 0% | 0% | 0% | 0% |
| | Mitomycin C (0.5 mg/kg/day) | 100% | 35% | 0% | 0% | 0% |
| Lymphotoxin mixture | 300 units/kg/day | 100% | 40% | 0% | 0% | 0% |
| | 1,000 units/kg/day | 100% | 45% | 45% | 30% | 30% |
| | 3,000 units/kg/day | 100% | 70% | 65% | 65% | 65% |
| | 10,000 units/kg/day | 100% | 100% | 85% | 85% | 85% |

EXPERIMENT C-5

Acute toxicity

An acute toxicity test, wherein a group of 20-day old mice were administrated with a lymphotoxin mixture, obtained similarly as in Example A-9, confirms that the toxicity of the lymphotoxin mixture is extremely low, i.e., LD$_{50}$, 10,000 units/kg or more, upon intraperitoneal injection.

The concentration of the lymphotoxin mixture required for 50% inhibition of in vitro cell multiplication was determined by the use of either normal human cells or human tumor cells in the usual way to give the following results: In normal human cells, e.g., human intestine cell (407 line), human Chang liver cells and Girardi Heart cells, the concentration is extremely high, i.e., 20,000 units/ml or higher, while in human tumor cells, e.g., KB cells of nasopharynx origin, HEp-2 cells of human larynx origin, HEL cells of lung carcinoma origin, the concentrations are extremely low, i.e., 18 units/ml, 24 units/ml, and 33 units/ml, respectively.

As obvious from the above experiment, the present TCLF is very safe and effective high dosage does not practically affect normal cells, while low dosage remarkably affects tumor cells; thus, it is favorably usable for treating various TCLF-sensitive diseases.

The dosage of the present TCLF generally falls in the range of 5–50,000,000 units per day for an adult; particularly, for local administration, e.g., in the form of collyrium or local injection, 5–1,000,000 units per day; for percutaneous or permucosal administration, e.g., in the form of ointment or suppository, 10–5,000,000 units per day; for systemic administration, e.g., intravenous- or intramuscular injection, 50–10,000,000 units per day;

and oral administation, 500–50,000,000 units per day, but is freely variable dependent upon its instructions and the patient's symptoms.

Although the TCLF may be, if necessary, prepared into a medicine in usual way after admixing with a conventional carrier, base and/or vehicle, the TCLF content thereof should be at least 5 units per g in view of its toxicity, effective dosage, and stability.

The shape and form of the medicine for malignant tumor may be freely chosen as far as the objectives can be attained; for example, for oral administration, it may be shaped into certain preparations for enteric uses, e.g., capsule, tablet or powder; for rectal administration, suppository; for injection, it may be, for example, prepared into a lyophilized injection which is dissolved, prior to use, into an injection solution with distilled water, as well as in the forms of collunarium, collyrium, or ointment.

The following Examples illustrate the agents containing TCLF, but it will be intended in no way to limit the scope of the invention.

EXAMPLE B-1

Injection

A lymphotoxin solution, prepared by dissolving 20,000 units of a lymphotoxin mixture, obtained similarly as in Example A-9, into 200 ml physiological saline solution, was filtered under sterile conditions with the use of a membrane filter. Two ml aliquots of the filtrate were distributed into sterilized glass vials, lyophilized, and packed therein to obtain the titled product.

The injection is favourably usable for treating breast cancer, lung carcinoma, liver carcinoma, and leukaemia.

EXAMPLE B-2

Ointment

A lymphotoxin mixture, obtained similarly as in EXAMPLE A-3, was admixed with a minimal amount of liquid paraffin, and the mixture was further admixed with vaseline to obtain an ointment with a lymphotoxin content of 50 units per g, in usual way.

The ointment is favorably usable for treating skin carcinoma, breast cancer, or lymphoma.

EXAMPLE B-3

Collyrium

A mixture, consisting of 800 ml distilled water, 5 ml β-phenylethyl alcohol, and 40,000 units of a lymphotoxin mixture, obtained similarly as in Example A-6, was admixed with sodium chloride in an additional amount of distilled water to obtain 1,000 ml of an isotonic solution.

The resultant solution is favorably usable as a collyrium for treating retinoblastoma.

EXAMPLE B-4

Enteric coated tablet

An enteric coated tablet was prepared according to conventional methods by tabletting an admixture consisting of starch, maltose, and a lymphotoxin preparation with a molecular weight of $1 \times 10^4$–$2 \times 10^4$ daltons, obtained similarly as in EXAMPLE A-9, to give a lymphotoxin content of 2,000 units per tablet (100 mg), followed by coating the tablet with phthalate ester of methyl cellulose to obtain the titled product.

The tablet is favorably usable for treating colon carcinoma, and liver carcinoma.

EXAMPLE B-5

Injection

A TNF solution, prepared by dissolving 500,000 units of a TNF preparation, obtained in Example A-10, into 200 ml physiological saline solution, was filtered under sterile conditions with the use of a membrane filter. Two ml aliquots of the filtrate were distributed into sterilized glass vials, lyophilized, and packed therein to obtain the titled product.

The injection is favorably usable for treating breast cancer, lung carcinoma, liver carcinoma and leukaemia.

EXAMPLE B-6

Ointment

A TNF preparation, obtained in Example A-11, was admixed with a minial amount of liquid paraffin, and the mixture was further admixed with vaseline to obtain an ointment with a TNF content of 20,000 units per g in usual way.

The ointment is favorably usable for treating skin carcinoma, breast cancer, and lymphoma.

EXAMPLE B-7

Collyrium

A mixture, consisting of 800 ml distilled water, 5 ml β-phenylethyl alcohol, and 20,000,000 units of a TNF preparation obtained in Example A-14, was admixed in an additional amount of distilled water with sodium chloride to obtain 1,000 ml of an isotonic solution.

The solution is favorably usable as a collyrium for treating retinoblastoma.

EXAMPLE B-8

Enteric coated tablet

An enteric coated tablet was prepared according to conventional methods by tabletting an admixture, consisting of starch, maltose, and a TNF preparation, obtained in Example A-12, to give a TNF content of 200,000 units per tablet (100 mg), followed by coating the tablet with phthalate ester of methyl cellulose to obtain the titled product.

The tablet is favourably usable for treating colon carcinoma, and liver carcinoma.

We claim:

1. A process for producing human Target Cell Lysis Factor (TCLF), comprising:
   implanting a human cell line selected from the group of cell lines consisting of BALL-1, TALL-1, NALL-1, Namalwa, MOLT-3, Mono-1, B-7101, JBL, EBV-Sa, EBV-Wa, EBV-HO, BALM 2, CCRF-CEM, DND-41, and CCFR-SB in a non-human warm-blooded animal;
   feeding the animal to allow said human cell line to utilize the nutrient body fluid of the animal for its multiplication;
   exposing the multiplied human cells to a TCLF inducer under conditions appropriate to induce the accumulation of a substantial amount of TCLF by said cells; and
   recovering the accumulated TCLF.

2. A process in accordance with claim 1, wherein said exposing and recovering steps comprise:

extracting and disaggregating the human cell line tumor formed in the animal to obtain the multiplied human cells;

exposing the multiplied human cells to an effective amount of TCLF inducer on an in vitro culture medium under conditions appropriate to induce the accumulation of a substantial amount of TCLF; and recovering the accumulated TCLF from said culture.

3. A process in accordance with claim 1, wherein said TCLF inducer is a member selected from the group consisting of virus, nucleic acid, nucleotide, lectin, mitogen and endotoxin.

4. A process in accordance with claim 1, wherein said TCLF inducer is phytohaemagglutinin or concanavalin A.

5. A process in accordance with claim 1, wherein said TCLF is a glycoprotein with a molecular weight in the range of $1 \times 10^4 - 1 \times 10^5$ daltons and a saccharide content in the range of 5–45%.

6. A process in accordance with claim 1, wherein the TCLF contains at least one member of specimens having a molecular weight of about $1 \times 10^4 - 2 \times 10^4$ daltons, about $3.5 \times 10^4 - 5 \times 10^4$ daltons or about $7 \times 10^4 - 9 \times 10^4$ daltons.

7. A process as set forth in claim 1, wherein said TCLF contains a member selected from the group consisting of lymphotoxin, human Tumor Necrosis Factor (hTNF) and a mixture thereof.

8. A process for producing human Target Cell Lysis Factor (TCLF), comprising:

suspending a human cell line selected from the group of cell lines consisting of BALL-1, TALL-1, NALL-1, Namalwa, MOLT-3, Mono-1, B-7101, JBL, EBV-Sa, EBV-Wa, EBV-HO, BALM 2, CCRF-CEM, DND-41 and CCRF-SB in a diffusion chamber in which the nutrient body fluid of a non-human warm-blooded animal may be supplied to said human cell line;

embedding or placing said chamber in or on a non-human warm-blooded animal in a manner such that the nutrient body fluid of said animal is supplied to the cell line within said chamber;

feeding the animal to allow said human cell line to utilize said nutrient body fluid for its multiplication;

exposing the multiplied human cells to a TCLF inducer under conditions appropriate to induce the accumulation of a substantial amount of TCLF; and recoving the accumulated TCLF.

9. A process in accordance with claim 8, wherein said exposing and recovering steps comprise:

harvesting the multiplied human cells from said diffusion chamber;

exposing the harvested multiplied human cells to an effective amount of TCLF inducer on an in vitro culture medium under conditions appropriate to induce the accumulation of a substantial amount of TCLF; and recovering the accumulated TCLF from said culture.

10. A process in accordance with claim 8, wherein said TCLF inducer is a member selected from the group consisting of virus, nucleic acid, nucleotide, lectin, mitogen and endotoxin.

11. A process in accordance with claim 8, wherein said TCLF inducer is phytohaemagglutinin or concanavalin A.

12. A process in accordance with claim 8, wherein said TCLF is a glycoprotein with a molecular weight in the range of $1 \times 10^4 - 1 \times 10^5$ daltons and a saccharide content in the range of 5–45%.

13. A process in accordance with claim 8, wherein the TCLF contains at least one member of specimens having a molecular weight of about $1 \times 10^4 - 2 \times 10^4$ daltons, about $3.5 \times 10^4 - 5 \times 10^4$ daltons or about $7 \times 10^4 - 9 \times 10^4$ daltons.

14. A process as set forth in claim 8, wherein said TCLF contains a member selected from the group consisting of lymphotoxin, human Tumor Necrosis Factor (hTNF) and a mixture thereof.

15. A process for producing human Tumor Necrosis Factor (nTNF), comprising:

culturing a human cell line capable of producing hTNF in the presence of an effective amount of a TNF inducer under conditions appropriate to induce the accumulation of a substantial amount of hTNF; and recovering hTNF.

16. A process in accordance with claim 15, wherein said culturing step comprises:

implanting a human cell line capable of producing hTNF in a non-human warm-blooded animal;

feeding the animal to allow said human cell line to utilize the nutrient body fluid of the animal for its multiplication; and exposing the multiplied human cells to a TNF inducer under conditions appropriate to induce the accumulation of a substantial amount of hTNF.

17. A process in accordance with claim 15, wherein said culturing step comprises;

suspending a human cell line capable of producing hTNF in a diffusion chamber in which the nutrient body fluid of a non-human warm-blooded animal may be supplied to said human cell line;

embedding or placing said chamber in or on a non-human warm-blooded animal in a manner such that nutrient body fluid of said animal is supplied to the cell line within said chamber;

feeding the animal to allow said human cell line to utilize said nutrient body fluid for its multiplication; and exposing the multiplied human cells to TNF inducer under conditions appropriate to induce the accumulation of a substantial amount of hTNF.

18. A process as set forth in claim 16, wherein said exposing and recovering steps comprise:

extracting and disaggregating the human cell line tumor, formed in the animal, to obtain the multiplied human cells;

exposing the multiplied human cells to an effective amount of TNF inducer on an in vitro culture medium under conditions appropriate to induce the accumulation of a substantial amount of hTNF; and recovering the accumulated hTNF from said culture.

19. A process in accordance with claim 15, wherein said exposing and recovering steps comprise:

harvesting the multiplied human cells from said diffusion chamber;

exposing the harvested multiplied human cells to an effective amount of TNF inducer on an in vitro culture under conditions appropriate to induce the accumulation of a substantial amount of hTNF; and recovering the accumulated hTNF from said culture.

20. A process in accordance with claim 15, wherein said human cell line is a human lymphoblastoid line.

21. A process in accordance with claim 15, wherein said human cell line is a member selected from the group of cell lines consisting of BALL-1, NALL-1, TALL-1, Namalwa, MOLT-3, Mono-1, B-7101, JBL, EBV-Sa, EBV-Wa, EBV-HO, BALM 2, CCRF-CEM and CCFR-CB.

22. A process in accordance with claim 15, wherein said TNF inducer is a member selected from the group consisting of virus, nucleic acid, nucleotide, lectin, mitogen and endotoxin.

23. A process in accordance with claim 15, wherein said TNF inducer is phytohaemagglutinin or concavalin A.

* * * * *